United States Patent [19]
Williams et al.

[11] Patent Number: 5,811,812
[45] Date of Patent: Sep. 22, 1998

[54] MULTIPLE-GAS NDIR ANALYZER

[75] Inventors: Kevin G. Williams, Pinole; Kim S. Christensen, Livermore, both of Calif.

[73] Assignee: Andros, Incorporated, Berkeley, Calif.

[21] Appl. No.: 743,411

[22] Filed: Nov. 1, 1996

[51] Int. Cl.[6] .................................................. G01N 21/61
[52] U.S. Cl. ........................... 250/343; 96/4; 250/339.13; 356/440
[58] Field of Search ............................. 250/343, 339.13; 356/440; 96/4

[56] References Cited

U.S. PATENT DOCUMENTS

| | | | |
|---|---|---|---|
| 4,013,260 | 3/1977 | McClatchie et al. | 250/343 |
| 5,049,170 | 9/1991 | Parnoff | 55/323 |
| 5,060,508 | 10/1991 | Wong | 73/31.02 |
| 5,332,901 | 7/1994 | Eckles et al. | 250/345 |
| 5,376,163 | 12/1994 | Carlson et al. | 95/22 |
| 5,384,640 | 1/1995 | Wong | 356/437 |
| 5,464,982 | 11/1995 | Drucker et al. | 250/343 |
| 5,572,032 | 11/1996 | Fujiwara et al. | 250/345 |

FOREIGN PATENT DOCUMENTS

| | | | |
|---|---|---|---|
| 5-115735 | 5/1993 | Japan | 96/4 |
| 6-226030 | 8/1994 | Japan | 96/4 |

*Primary Examiner*—Constantine Hannaher
*Attorney, Agent, or Firm*—Coudert Brothers

[57] ABSTRACT

A non-dispersive infrared (NDIR) multi-gas analyzer has an optical element that is positioned with respect to the axis of incident IR radiation such that it passes nearly all of the IR energy within a narrow band pass to one detector and reflects nearly all of the IR energy outside the narrow band pass to another detector. Thus, the optical element simultaneously functions both as a narrow band pass filter and a beam splitter, which transmits nearly all the IR energy within a band pass and reflects nearly all the IR energy outside the band pass. Additionally, the separation of the incoming energy can be achieved without an extended roll off. This allows using a reference transmission band that is very close to the absorption band of the gases of interest. It more specifically allows using a reference transmission band that is located between the absorption bands for hydrocarbons and carbon dioxide in an infrared analyzer that uses beam splitters.

19 Claims, 10 Drawing Sheets

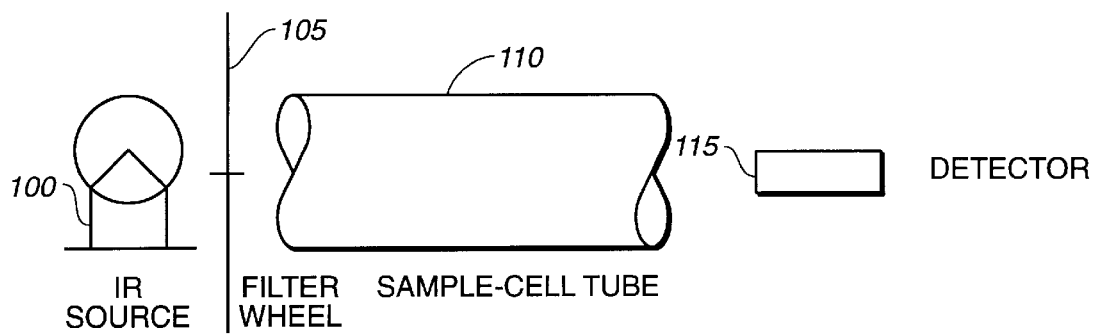
FIG. 1A *(PRIOR ART)*
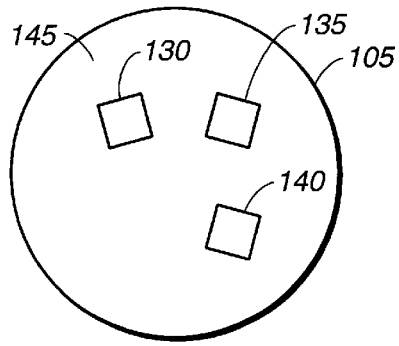
FIG._1B
*(PRIOR ART)*
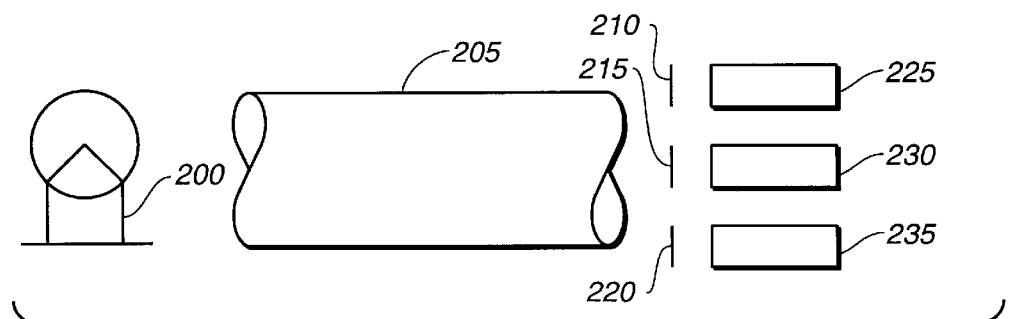
FIG._2 *(PRIOR ART)*
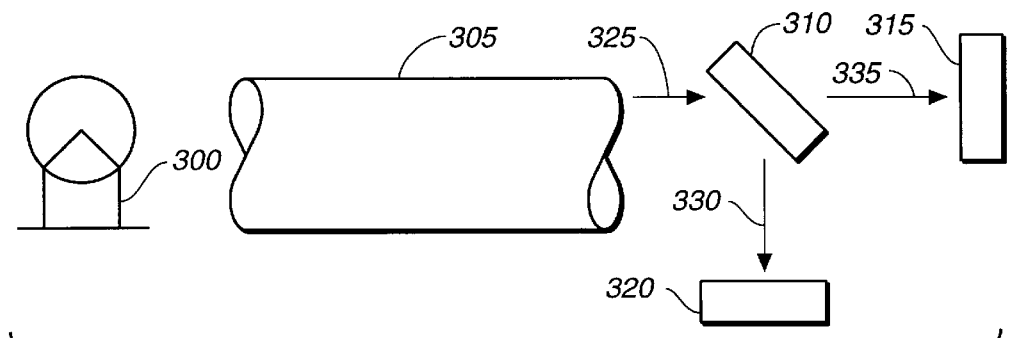
FIG._3 *(PRIOR ART)*

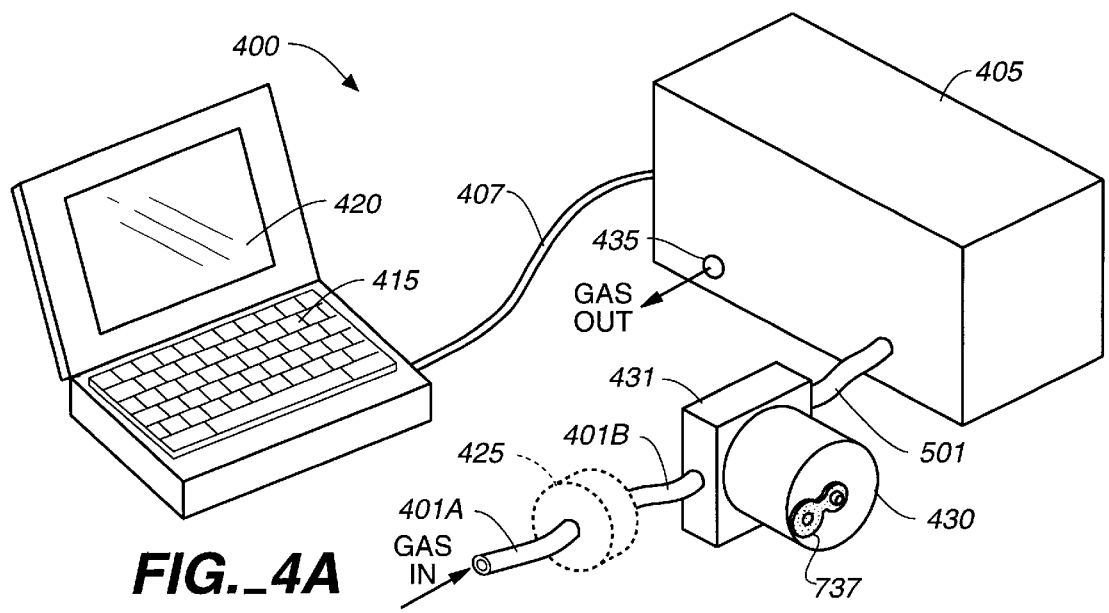
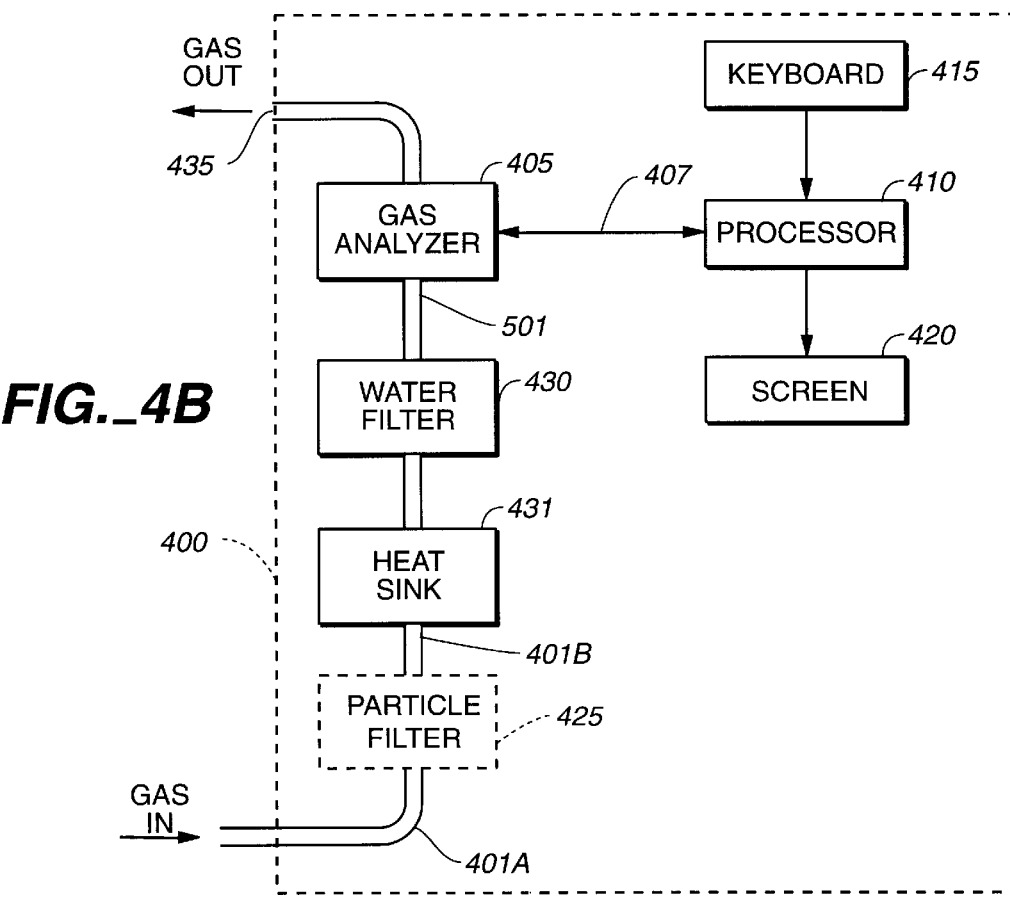

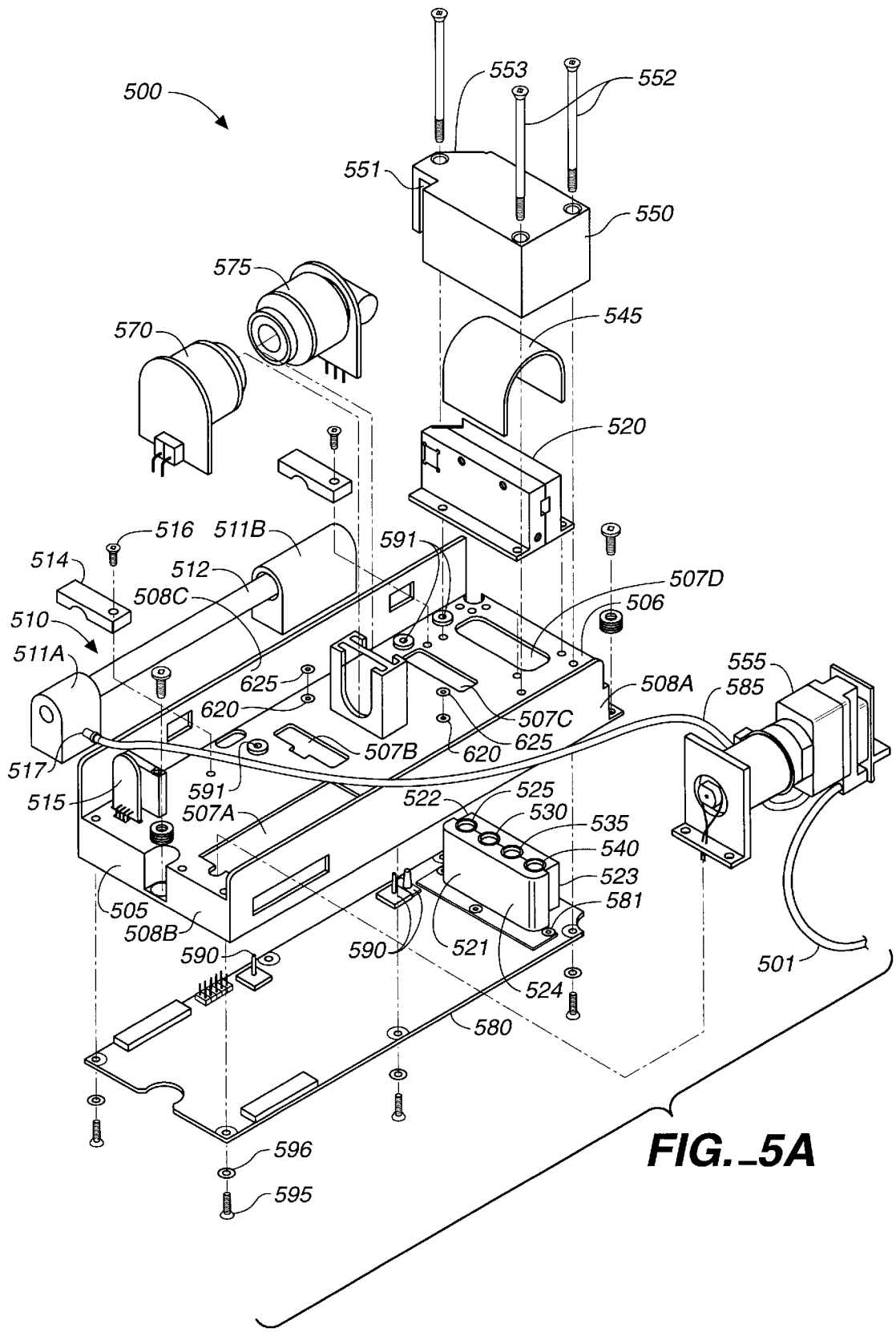
FIG._5A

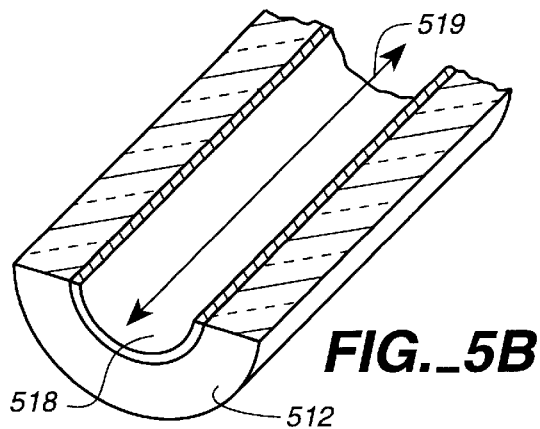
FIG._5B
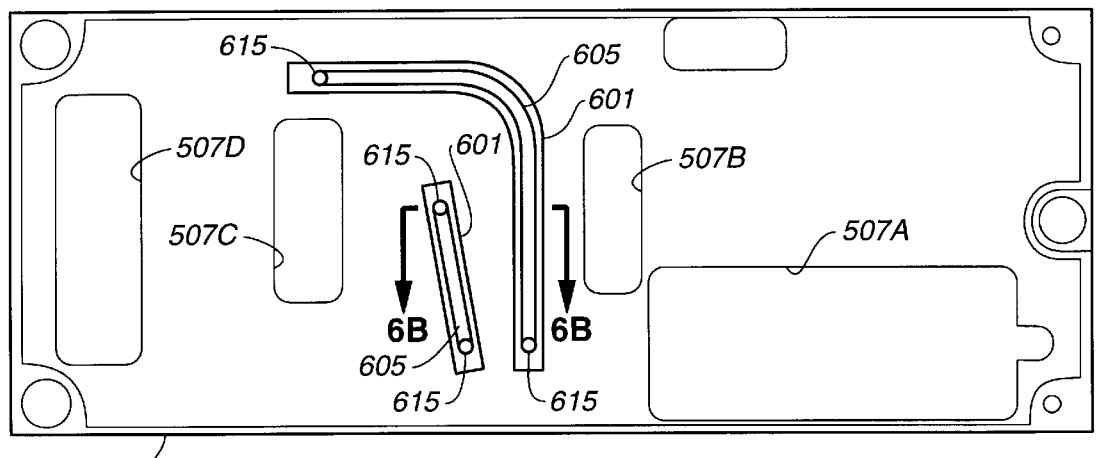
FIG._6A
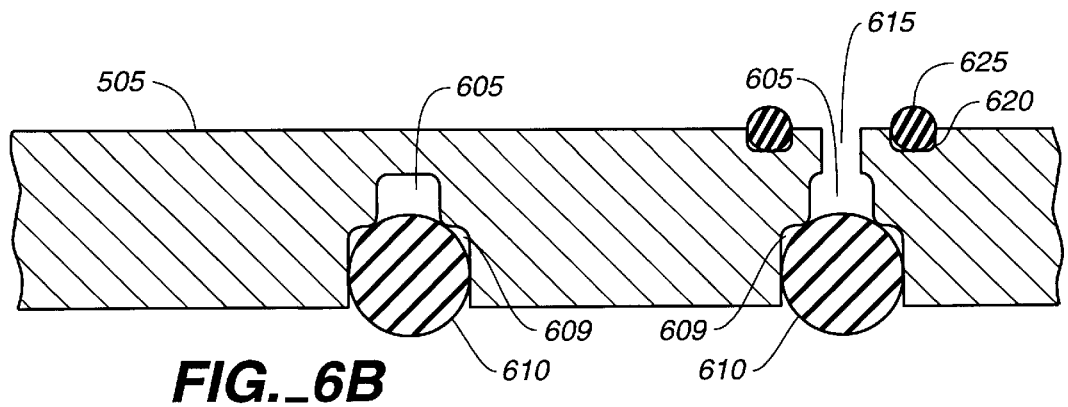
FIG._6B

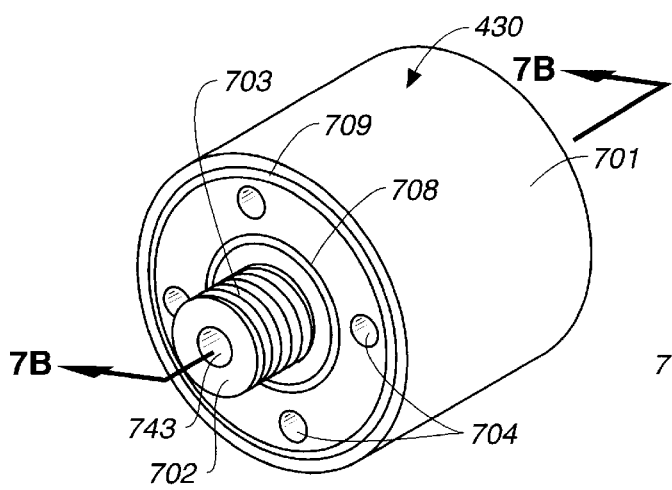
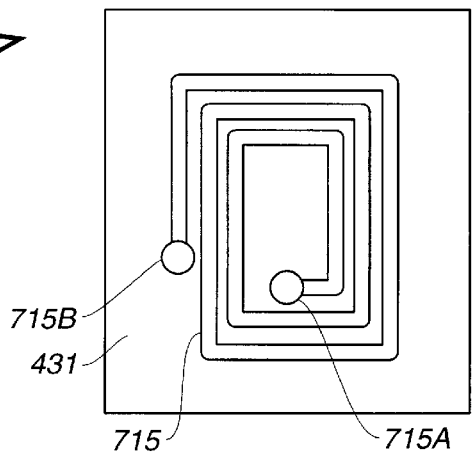
FIG._7A
FIG._7C
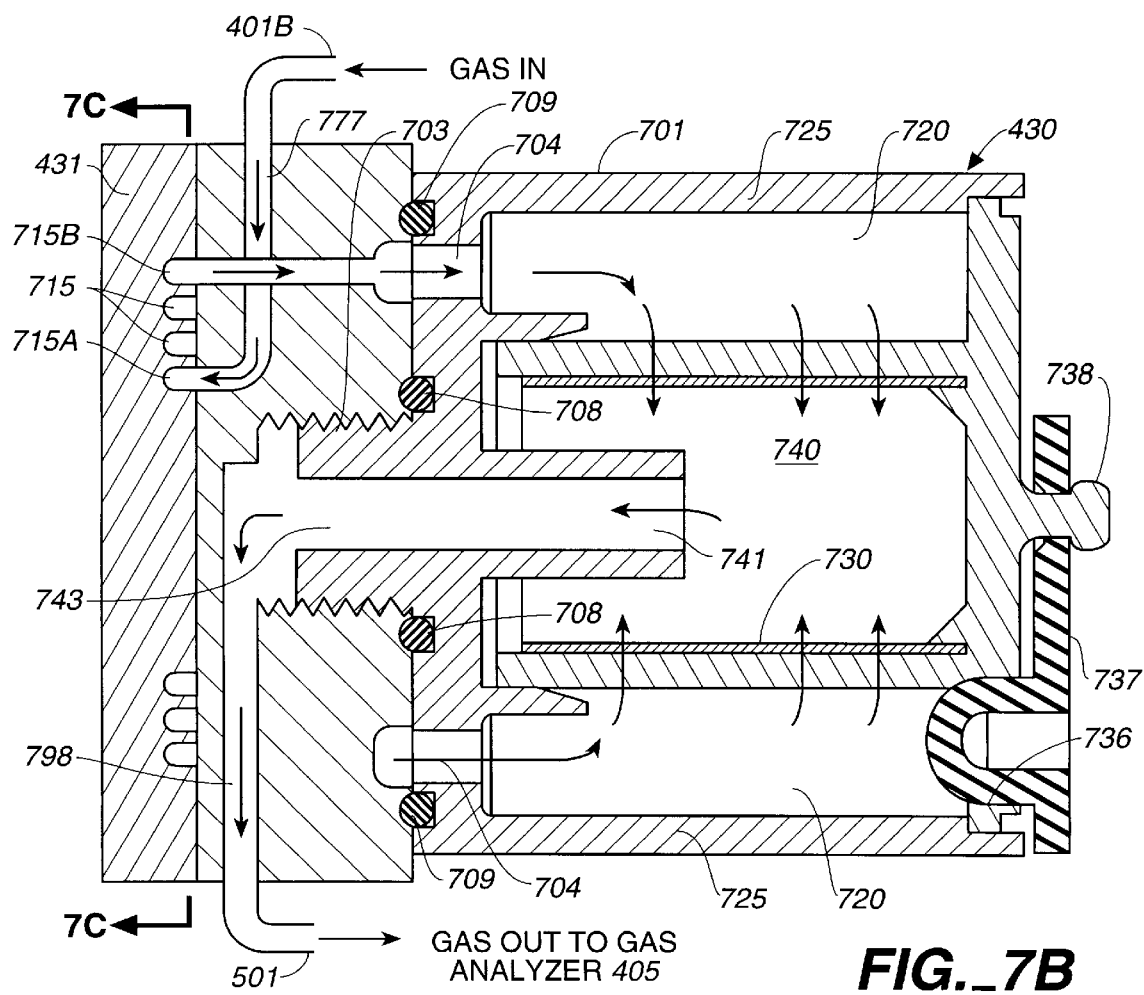
FIG._7B

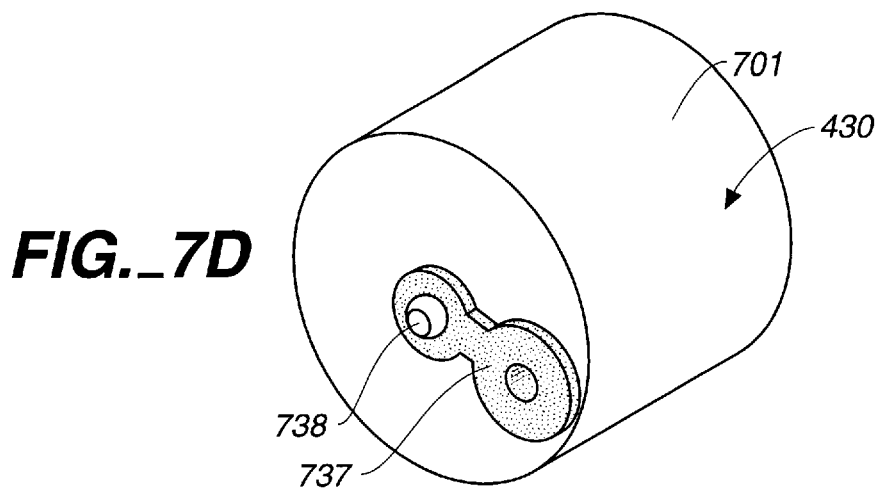
FIG._7D
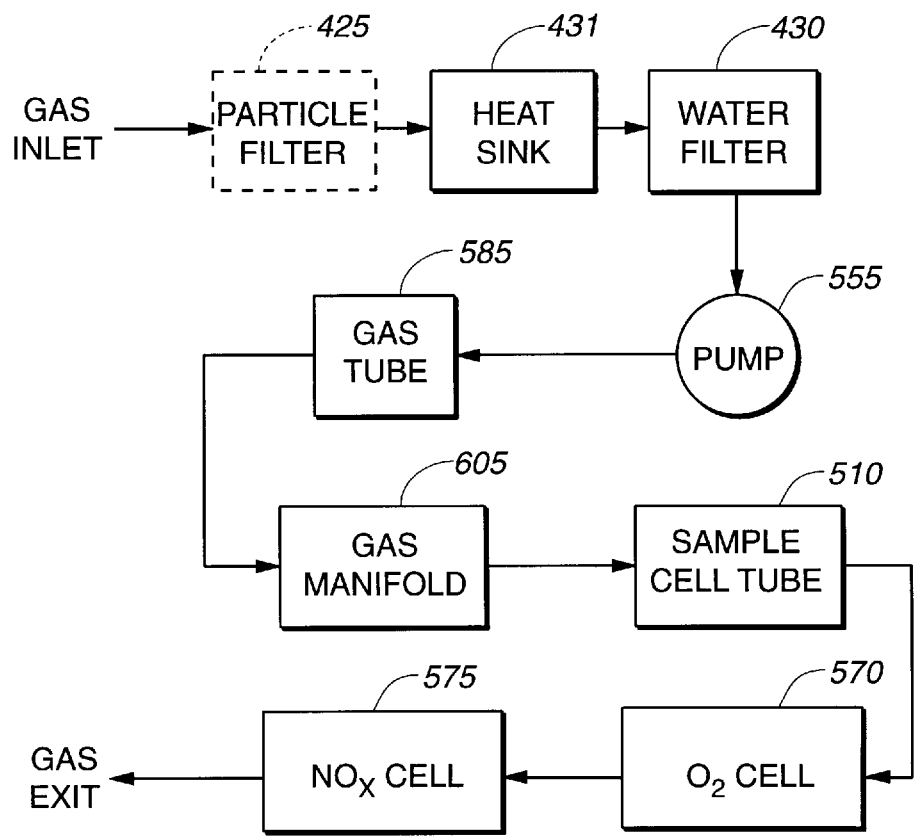
FIG._8

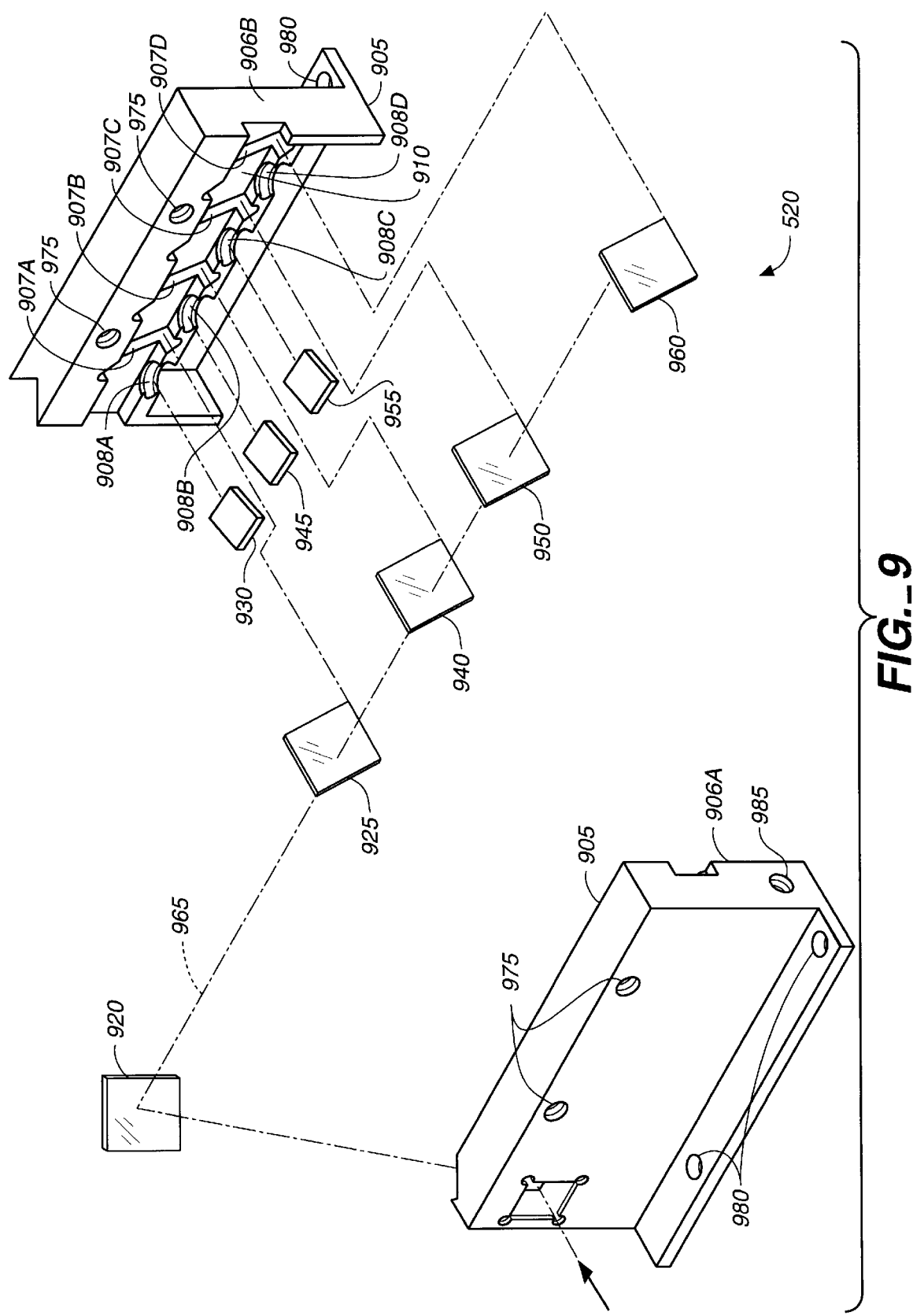
FIG._9

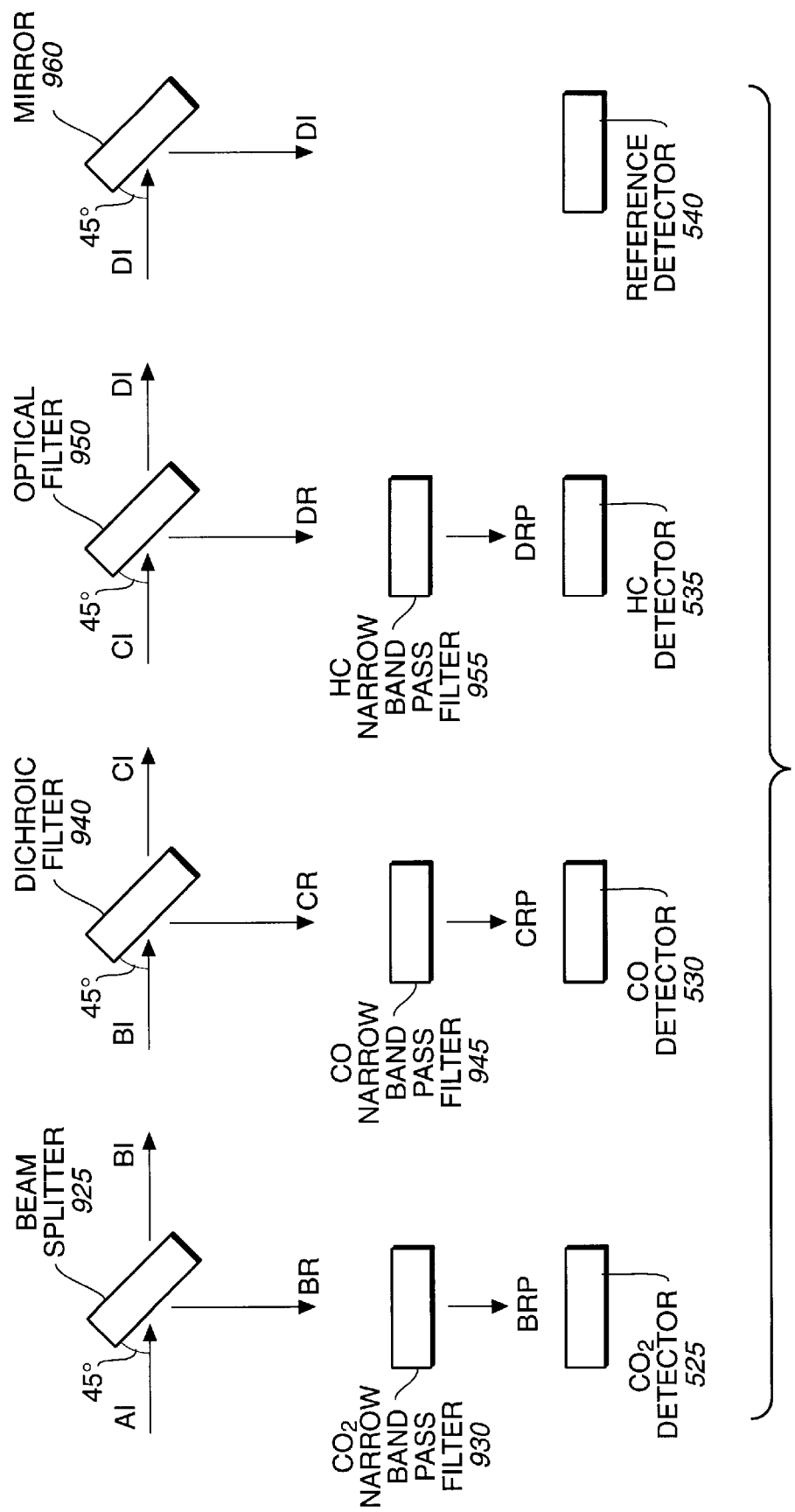
FIG._10

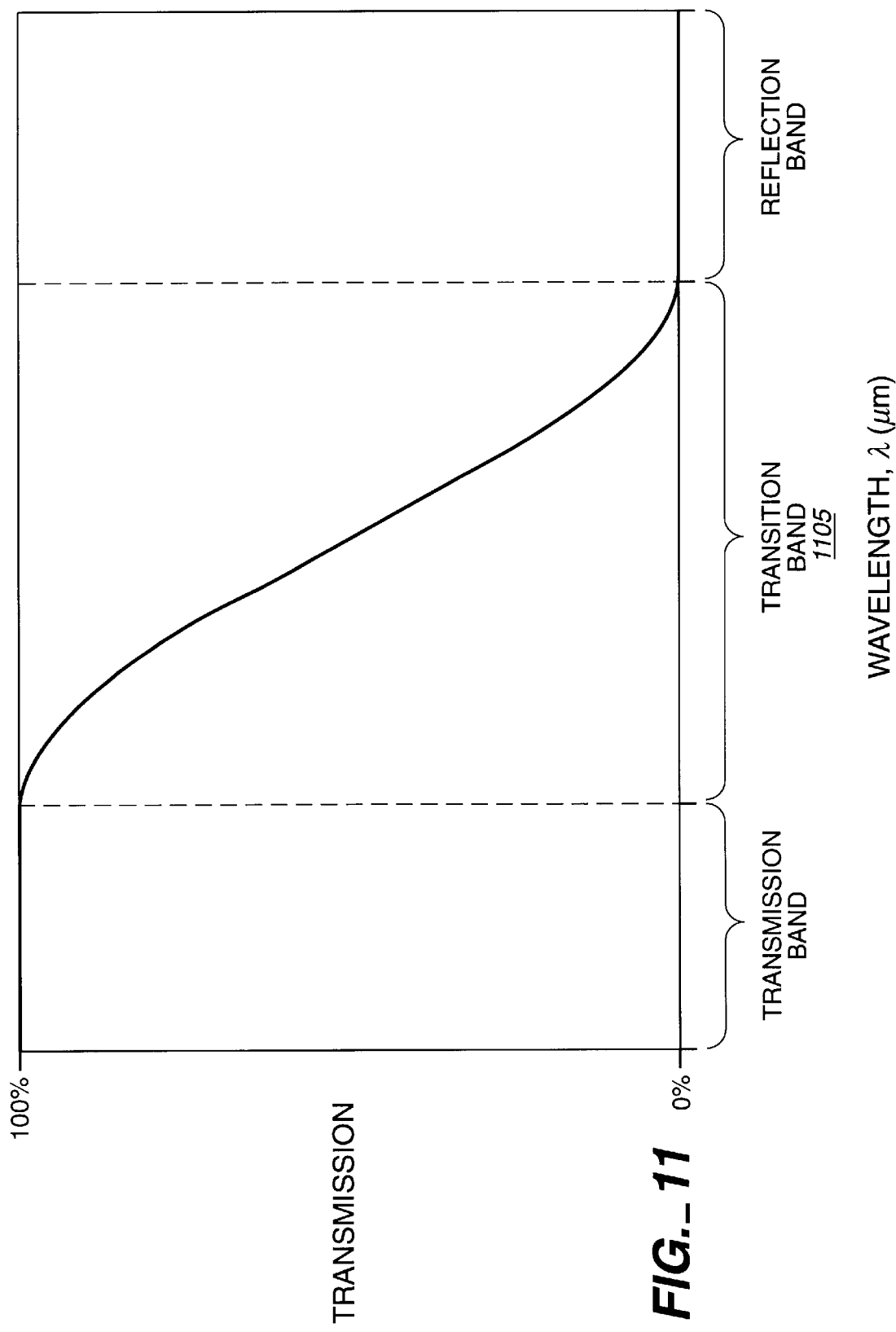
FIG._11

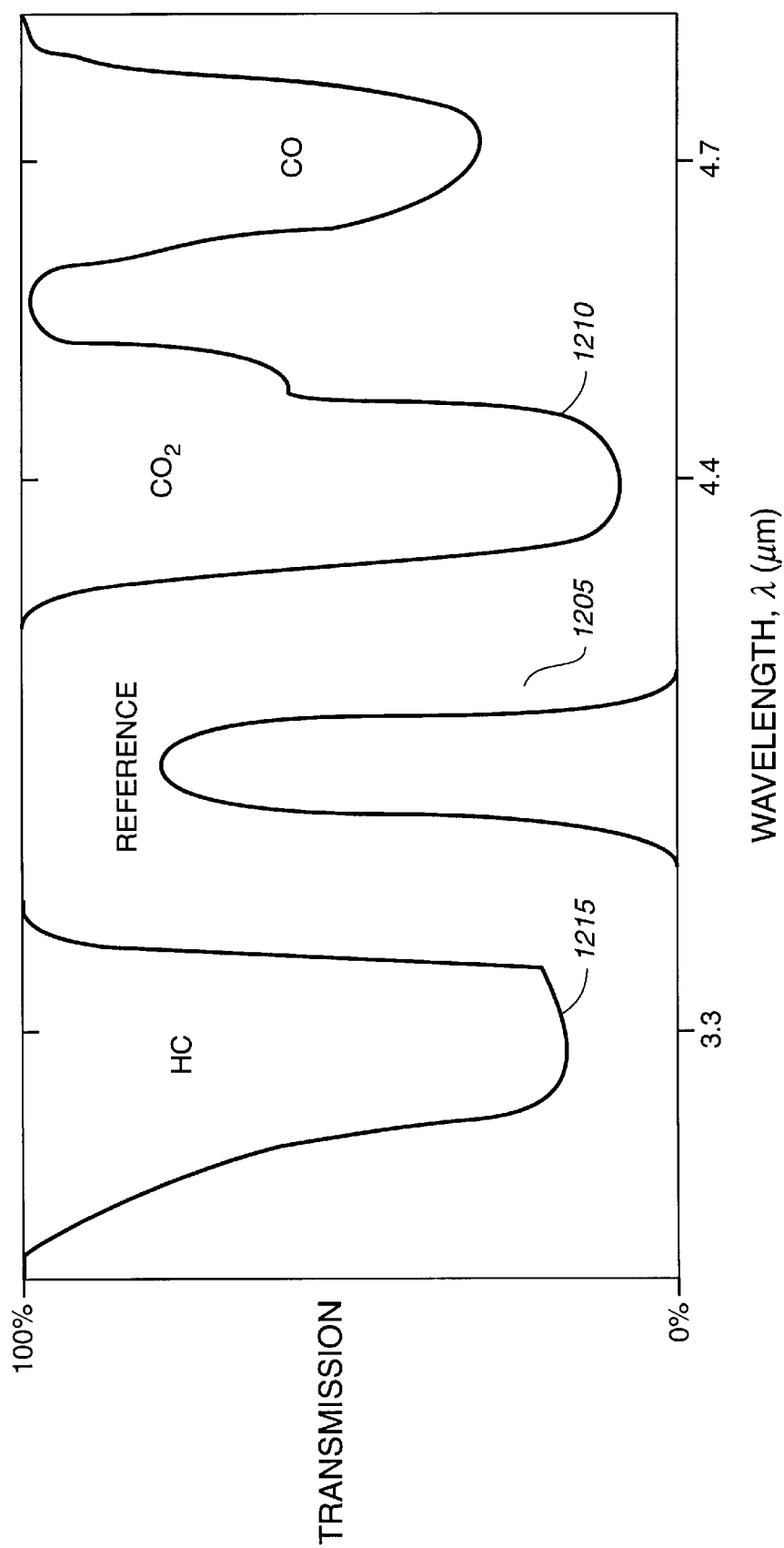
FIG._12

MULTIPLE-GAS NDIR ANALYZER

FIELD OF THE INVENTION

The present invention relates to infrared (IR) gas analyzers. More specifically, the present invention relates to multiple gas non-dispersive infrared (NDIR) analyzers.

BACKGROUND OF THE INVENTION

NDIR gas analyzers are generally known in the prior art. These analyzers utilize an IR source, typically an electric heater, to provide IR radiation through a gas sample contained in a sample cell for detection by a detector. The amplitude of the signal detected by the detector at a wavelength, which corresponds to the absorption wavelength of a gas of interest, provides an indication of the concentration of that gas in the sample. Concentration of gases, such as CO, $CO_2$, hydrocarbons (HCs), anesthetic agent gases, exhaust gases, Freon, or other gases can be determined by IR radiation spectroscopes. Each species of gas typically has one or more distinct IR absorption characteristics and better absorbs IR radiation at or near a particular wavelength. The absorption of IR radiation at a frequency corresponding to a characteristic absorption wavelength of a particular gas species is directly related to the concentration of that species in the gas sample. In other words, the amplitude of the signal detected by the IR detector at a wavelength corresponding to a characteristic absorption wavelength of a particular gas species is inversely proportional to the concentration of that species in the gas sample.

The reading at the detector is subject to system sensitivities which are independent of gases within the gas sample. Such system sensitivities include absorption by contaminants on the gas sample cell windows, IR dissipation due to obstructions in the radiation path, effectiveness of the manner by which the radiation is collected after passing through the sample cell, the sensitivity of the detector, and the gain of the signal processing electronics. In order to account for system sensitivities in the concentration readings, a reference detector is used. The reference detector is intended to provide a measure of the intensity of the infrared radiation in the optical path at a wavelength which is unaffected by the presence of gases likely to be in the sample cell. Therefore, the detector signal measured by the reference detector provides a measure of the basic sensitivity of the system to infrared radiation in general. That is, it provides a measure of the strength of the radiation of the IR source, the attenuation of the radiation by (non-spectral) contamination and the like on the infrared transparent windows in the sample cell tube, and further provides a measure of the effectiveness of the collector and the sensitivity of the detectors as well as the gain of the processing electronics.

The band width and the center of the band for the reference detector are selected to be in an infrared non-absorptive region for typical gas samples to be tested. Otherwise, the reading by the reference detector would be influenced by the concentration of any gases in the gas sample which absorb IR radiation before it reaches the reference detector. Therefore, it is important that the reference detector detect IR radiation at a wavelength which is displaced from the absorption wavelengths of the gases likely to be present in the gas sample.

However, it is also important that the characteristic absorption wavelength at which the reference detector detects IR radiation not be widely spaced from the characteristic absorption wavelengths of the gases of interest. This is because some system sensitivities are highly dependent on the wavelength of IR radiation used. Therefore, it is preferable to use a reference wavelength that is close to, but does not overlap, the characteristic absorption wavelength of any of the gases of interest, to increase the likelihood that the reference is a true reference which is unaffected by the concentration of the gases in the gas sample.

The prior art NDIR analyzers operate under the general principles outlined above and fall under three general groups: (1) Single path analyzers with a filter wheel; (2) Single path analyzers without a filter wheel; and (3) Multiple path analyzers.

FIGS. 1A and 1B show a schematic diagram of a single path analyzer with a filter wheel and a face view of the filter wheel, respectively. The analyzer shown in FIG. 1A includes an IR radiation source 100, a sample cell tube 110, a filter wheel 105 and a detector 115. The IR radiation source 100 emits an IR radiation (not shown) that is filtered by the filter wheel 105 before it passes through the sample cell tube 110.

As shown in FIG. 1B, the filter wheel has a plurality of band pass filters that preferentially allow incident IR energy to be transmitted into the sample cell at a selected IR wavelength range. The filter wheel is periodically rotated to place one of the band pass filters in the path of the IR radiation exiting the sample cell tube 110. As the filter wheel is rotated, it alternately totally blocks radiation, passes radiation in a wave length band (the reference band) which will not be absorbed by a random gas sample, and sequentially passes radiation in one or more additional bands which will be absorbed by one or more gases in the sample cell. The blocking segment 145 is utilized to block the source radiation from the sample cell so that the detector signal may be used to indicate combined effects such as background radiation, detector null, electronic offsets, etc. The reference filter 130 is used to transmit IR radiation at the reference wavelength to provide a measure of the basic sensitivity of the system to IR radiation in general. The remaining filters 135 and 140 pass IR radiation that will be absorbed by gases in the gas sample.

The IR radiation transmitted to the sample cell tube is absorbed by any gases whose absorption characteristics correspond to the wavelength of the IR radiation transmitted through the filter wheel 105. The degree of IR radiation absorption in the sample cell tube 110 is directly proportional to the concentration of the absorbing gas. Therefore, the higher the concentration of the absorbing gas, the greater the absorption of the IR radiation in the sample cell tube 110. The portion of the IR radiation that is not absorbed by any gases in the sample cell or other system sensitivity producing substances, such as contaminates on the sample cell windows (not shown), passes out of the sample cell tube 110 and is transmitted to the detector 115. The detector 115, therefore, detects the portion of the IR radiation transmitted by the source, which is not absorbed by either gases in the sample cell or other system absorbents. The detector 115 provides a measure of the concentration of each gas species of interest as well as a reference reading. When the filter wheel passes IR radiation corresponding to the absorption wavelength of a gas species of interest, then the reading of the detector provides a measure of the concentration of that gas species. Similarly, when the filter wheel passes IR radiation corresponding to the reference wavelengths, then the detector provides a reference reading.

The NDIR analyzer described above suffers from several limitations. First, the filter wheel is a moving part that contributes to reliability problems. It is preferable to have as few moving parts as possible so as to increase the reliability of the system. Second, the filter wheel requires power for rotating the wheel which increases the operating power for the analyzer. Third, because the filter wheel has more than one filter, and the filters are interposed in the IR path sequentially, the effective duty-cycle for measuring IR absorption by a particular gas or by the system sensitivities is intermittent. Consequently, the signal received for a particular concentration reading is not as strong as it would be if the detector were used for making that particular reading continuously. Therefore, a lower effective duty-cycle results in a weaker signal which in turn results in a lower signal to noise (S/N) ratio.

Some of the above disadvantages of the filter wheel type of IR analyzers are eliminated by the second type of analyzer, namely single path analyzers without a filter wheel, a schematic diagram of which is shown in FIG. 2. As shown in FIG. 2, the NDIR analyzer of the second type includes an IR radiation source 200, a sample cell tube 205, measurement detectors 225 and 230, a reference detector 235 and interference filters 210, 215, and 220 interposed between the sample cell-tube 205 and the detectors 225, 230, and 235. The sample cell tube 205 is placed in the path of IR radiation emanating from IR radiation source 200. Similarly, interference filters 210, 215 and 220 are disposed in the path of IR radiation that exits sample cell tube 205. Finally, detectors 225, 230 and 235 are disposed in the path of IR radiation that passes through interference filters 210, 215 and 220, respectively.

The arrangement in FIG. 2 eliminates the need for a filter wheel since each detector is provided with its own band-pass filter, i.e. interference filters 210, 215 and 220, which transmits IR radiation to be detected by the detector. This deals with the disadvantages of the first NDIR analyzer type relating to the use of the filter wheel, namely lower reliability, higher operating power and lower effective duty-cycle. However, the second type of NDIR analyzers also have low S/N ratios. The low S/N, in this case, is not caused by a low effective duty-cycle since each detector is continuously exposed to IR radiation within a particular wavelength range. Instead, the low S/N ratio is caused by the sharing of the sample cell's cross sectional area by the measurement detectors and the reference detector. Sharing the sample cell's cross sectional area exposes each detector to less than the entire IR radiation received from the sample cell. Consequently, the signal received at each detector is weaker than it would be if the sample cell's cross sectional area were not shared with other detectors.

A third type of NDIR analyzer deals with the above disadvantages. However, it suffers from its own disadvantages. A schematic diagram of the third type of NDIR analyzer is shown in FIG. 3. As shown in FIG. 3, the analyzer contains an IR source 300, a sample cell tube 305, a beam splitter 310, a reference detector 315 and a measurement detector 320. Beam splitter 310 is disposed in the path of the IR radiation exiting sample cell tube 305. Beam splitter 310 receives IR radiation 325, reflects a first portion 330 thereof to detector 320, and transmits a second portion 335 thereof to detector 315. This setup effectively deals with the low intensity signal problems associated with sharing the cross sectional area of the sample cell through which radiation is transmitted to the detectors, and with the limited duty cycle problem. The third type of analyzer, however, is limited in its ability to analyze more than one gas species if the beam splitter 310 is a neutral density beam splitter since in that case both the transmitted and reflected radiation suffer much losses in intensity. The first portion 330, i.e., the reflected portion, and the second portion 335, i.e., the transmitted portion, each contain approximately 50% of the energy of the incoming signal 325. Thus, use of a neutral density beam splitter degrades the S/N ratio by a factor of two. If one attempts to avoid this factor of two loss in S/N ratio by using a dichroic filter as the beam splitter 310, then the spectral separation of the two spectral regions of interest must be large enough to be outside the spectral region in which the dichroic filter changes from very high transmission to very high reflection, i.e. the transition band of the dichroic filter. If in addition to reducing the S/N ratio, one desires to use a reference transmission band located in the spectral separation between two spectral regions of interest, then the spectral separation must be sufficiently large to fit both the dichroic transition band and the reference transmission band. Unfortunately, the spectral separation between two spectral regions of interest is not always sufficiently large to fit both the dichroic filter transition band and the reference transmission band. For example, the spectral separation between the $CO_2$ and HC absorption bands is not large enough for fitting both a reference transmission band and a dichroic filter transition band. Therefore, a dichroic filter can not be used to transmit nearly all the IR radiation within the reference transmission band, which falls between the absorption bands of $CO_2$ and HCs, to a reference detector (via a narrow band pass that only transmits radiation within the reference transmission band) and reflect nearly all the IR radiation within the absorption band of HCs to a second detector. As a result, beam splitter infrared analyzers of the prior art did not allow for placing the reference transmission band between the absorption bands of $CO_2$ and HCs.

The present invention is intended to deal with the above disadvantages as well as others present in many prior art systems.

SUMMARY OF THE INVENTION

The present invention encompasses an infrared analyzer comprising a source of infrared radiation emanating infrared radiation onto an infrared radiation path; a sample cell tube for containing an analyte gas disposed in the path of infrared radiation emanating from the source; and detector means positioned in the path of infrared radiation after passing through the sample cell for providing an indication of the absorption of infrared radiation by the analyte gas, where the detector means comprises (a) a first infrared radiation detector, (b) a second infrared radiation detector, and (c) at least one narrow band pass optical filter oriented to transmit infrared radiation within a narrow wavelength band to the first infrared radiation detector and to reflect infrared radiation outside of the narrow wavelength band to the second infrared radiation detector, whereby the first infrared radiation detector provides an indication of infrared radiation absorption by the analyte gas within the narrow wavelength band and wherein the second infrared radiation detector provides an indication of infrared absorption by the analyte gas outside of the narrow wavelength band.

The narrow band pass optical filter described above allows passing nearly all of the incident IR radiation within the narrow wavelength band pass to the first infrared radiation detector and reflecting nearly all of the IR radiation outside the narrow wavelength band pass to the second infrared radiation detector. Thus, the novel positioning of the optical element with respect to the axis of incident IR radiation allows the optical filter to simultaneously function both as a narrow band pass filter and a beam splitter. However, the beam splitting of the above optical filter is unlike that of a dichroic filter as the beam splitting is done without an extended roll off present in the beam splitting by dichroic filters. This is due to the fact that the transition band of the above optical filter is much smaller than the transition band of dichroic filters. The beam splitting of the above optical filter is also unlike the beam splitting of a neutral density beam splitter. A neutral density beam splitter both passes and reflects substantially identical signals. Each of the passed (transmitted) and reflected signals cover the same wavelength range as the incident signal and contain approximately 50% of the energy contained in the incident signal. On the other hand, the above optical filter as positioned in the present invention, splits the incoming signal by passing nearly all of the incident energy within a narrow band pass and reflects nearly all of the incident energy outside the narrow band pass.

Therefore, the narrow band pass optical filter as positioned in the present invention (i.e. at 45 degrees with respect to the axis of incident IR radiation) allows picking up nearly a 100% of the radiation within a desired wavelength band for analysis at a first stage and passing nearly a 100% of a second desired wavelength band for analysis at a second stage. Additionally, the novel positioning of the narrow band pass filter at 45 degrees with respect to the axis of incident IR radiation allows that such a separation of the incoming energy be achieved without an extended roll off. This allows using a reference transmission band that is very close to the absorption band of the gases of interest. It more specifically allows using a reference transmission band that is located between the absorption bands for hydrocarbons and carbon dioxide in a infrared analyzer that uses beam splitters. As discussed in the prior art section, it is desirable to use a reference band that is very close to but does not overlap the absorption wavelength bands for gas species in the sample gas so as to better match the reference reading with the system sensitivities to infrared radiation in the absorption wavelength bands in which the system operates.

Moreover, the NDIR of the present invention includes an arrangement of the detectors such that they need not share the area corresponding to the cross sectional area of the sample cell tube. This allows signals of greater intensity to be received by the detectors and consequently improves the signal to noise (S/N) ratio.

Additionally, in a preferred embodiment, the present invention includes an optical housing, which is also referred to as a common mechanical mounting platform, which can be fabricated from any suitable material including glass or plastic, to minimize adverse affects that would otherwise result from the differential thermal expansions/contractions and mechanical shock, vibrations and disturbances of the system components. The optical housing also acts as a light pipe as its interior infrared radiation reflecting surfaces are coated with highly reflective materials, such as gold, to further maximize the amount of infrared radiation incident on the detectors.

In a preferred embodiment, the NDIR analyzer also includes gas passages that are molded into the base plate frame of the analyzer so as to reduce the number of components, specifically gas tubings, used in the analyzer.

Accordingly, it is an object of the present invention to allow each detector channel, i.e. all measurement detectors and the reference detector, to effectively be exposed to the maximum available cross-sectional area defined by the geometry of the sample cell tube. Such an arrangement allows the detectors to receive infrared signals of greater intensity and consequently improves the signal level and the S/N ratio.

It is another object of the present invention to provide an optical element that operates both as a narrow band pass filter and a beam splitter to allow the reference band to be placed between the absorption bands for carbon dioxide and hydrocarbons.

It is another object of the present invention to provide for a spatial arrangement of optical components in which only the radiation needed at a particular detector is "picked-off" by the detector allowing the remaining radiation to pass to the next optical stage with little effective degradation or attenuation.

Another object of the invention is to provide an optical housing for the invention's optical components or elements, where the optical housing both acts as a lightpipe and reduces adverse effects that would otherwise result from differential thermal expansions/contractions and mechanical shock vibrations and disturbances.

Another object of the present invention is to provide for an arrangement of gas passages within the base plate of the analyzer to reduce the number of components in the system.

It is yet another object of the present invention to reduce the power required to operate the NDIR analyzer.

These and other objects of the present invention will become apparent to those skilled in the art from the following detailed description of the invention, the accompanying drawings, and the appended claims.

BRIEF DESCRIPTION OF THE DRAWINGS

FIG. 1A is a schematic diagram of a first prior art non-dispersive infrared analyzer.

FIG. 1B is a face view of the rotating filter wheel of FIG. 1A.

FIG. 2 is a schematic diagram of a second prior art non-dispersive infrared analyzer.

FIG. 3 is a schematic diagram of a third prior art non-dispersive infrared analyzer.

FIG. 4A is a perspective view of a gas analyzer module set of the present invention.

FIG. 4B is a schematic diagram of the gas analyzer module set of the present invention.

FIG. 5A is a perspective exploded view of the gas analyzer in the gas analyzer module set shown in FIG. 4.

FIG. 5B is a cut away perspective view of the lower half of the sample cell tube in FIG. 5A.

FIG. 6A is a plan view of the bottom surface of the base plate of the gas analyzer shown in FIG. 5.

FIG. 6B is a cross sectional view of the base plate along line 6B'—6B' of FIG. 6A.

FIG. 7A is a front perspective view of the water filter of the present invention.

FIG. 7B is a cross sectional view of the water filter along lines 7B'—7B' of FIG. 7A and the heat sink to which the water filter is coupled.

FIG. 7C is a top plan view of the heat sink of the present invention.

FIG. 7D is a rear perspective view of the water filter of the present invention.

FIG. 8 is a schematic diagram of the path of the gas analyzed in the gas analyzer module set shown in FIG. 4A.

FIG. 9 is a perspective exploded view of the optical block of the gas analyzer shown in FIG. 5A.

FIG. 10 is a schematic representation of the optical components and detectors of the present invention.

FIG. 11 is a graph of the absorption characteristics of a dichroic filter.

FIG. 12 is a graph of the absorption bands for several gases and the reference transmission band used in the present invention.

DETAILED DESCRIPTION OF THE DRAWINGS

FIGS. 4A and 4B show a perspective view and a schematic diagram of the gas analyzer module set 400 of the present invention, respectively. Gas analyzer module set 400 is also referred to as a minibench gas analyzer set 400. Gas analyzer module set 400 comprises gas analyzer 405, processor 410 coupled to the gas analyzer 405, keyboard 415, and screen 420 both of which are coupled to the processor 410. The gas analyzer 405 is coupled to the processor 410, keyboard 415 and screen 420 by wire 407, which may comprise a plurality of wires. Gas analyzer module set 400 also optionally comprises particle filter 425 shown in phantom. Particle filter 425 receives analyte gas from tube 401A and filters out particles from the analyte gas. Particle filters for removing particulate matter from gases, such as particle filter 425 are known in the art. Therefore, particle filter 425 will not be described in further detail herein. Particle filter 425 is coupled to heat sink 431 by tube 401B. The gas analyzer module set 400 also includes water filter 430 which is coupled to heat sink 431. Analyte gas that has passed through heat sink 431 and water filter 430 enters the gas analyzer 405 by way of tube 501, which is coupled to tube 798 (shown in FIG. 7B) that is disposed between water filter 430 and heat sink 431. It is to be noted that keyboard 415 and screen 420 are only exemplary input and output elements (also referred to as user interface elements). Accordingly, in other embodiments of the present invention, either the keyboard 415, the screen 420 or both the keyboard 415 and the screen 420 may be replaced by other input or output elements. Processor 410 is a conventional electronic processor that accepts input data from the gas analyzer and outputs corresponding data to the screen 420. Use of a general processor modified for use with a gas analyzer or one specifically designed for use with a gas analyzer is well known in the art. Therefore, the processor 410 will not be described in detail herein. The gas analyzer module set 400 also includes exhaust 435 through which analyzed gas exits the gas analyzer module set 400.

FIG. 5A shows a detailed exploded perspective view of gas analyzer 500 of the present invention. Gas analyzer 500 includes base plate 505. Base plate 505 has rectangular base 506 which has a number of generally rectangular perforations 507A, 507B, 507C and 507D, which are used for the placement of certain components, to be described below, of the gas analyzer 500. Base plate 505 also has side panels 508A, 508B and 508C, which are generally rectangular and perpendicular to rectangular base 506.

The gas analyzer 500 also includes gas pump 555, $O_2$ chemical cell 570 and $NO_x$ chemical cell 575, which are at least partially fitted into perforations 507A, 507B and 507C, respectively. Gas pump 555 pumps the gas entering into the gas analyzer to other elements within the gas analyzer, such as sample cell tube 510. In the present invention, pumping pressure rather than suction is used to transfer the analyte gas from one point to another so as to reduce intake of contaminant gases through possible leakages in the gas path of the gas analyzer. $O_2$ chemical cell 570 and $NO_x$ chemical cell 575 are used to measure the concentration of $O_2$ and $NO_x$ in the analyte gas. Gas pump 555, $O_2$ chemical cell 570 and $NO_x$ chemical cell 575 are conventionally used in gas analyzers and are well know to those skilled in the art. Therefore, they will not be described in greater detail herein so as not to detract from the present invention.

The gas analyzer 500 also includes the detector block 524 which is inserted into the perforation 507D in base plate 505. Detector block 524 comprises segments 521, 522 and 523, each of which has half cylindrical indentations therein. Detector block 524 is assembled by attaching segments 522 and 523 to segment 521 by use of screws (not shown) after aligning the half cylindrical indentations in segments 522 and 523 with those of segment 521. The assembled detector block 524, therefore, has several full cylindrical perforations which are used for housing detectors 525, 530, 535 and 540. Detectors 525, 530 and 535 absorb IR radiation within the absorption bands for $CO_2$, CO and HC, respectively. Detector 540 absorbs IR radiation having wavelengths within the reference transmission band.

Since the system of the present invention is designed for lower operating power, it does not, unlike the prior art systems, expend additional energy to heat the elements in the system so as to maintain them at a desired temperature. Therefore, the temperature of the elements in the present invention are more likely to vary with ambient temperature variations. Consequently, the proper operation of the analyzer of the present invention requires use of detectors which function properly and consistently over a wide range of temperatures. Therefore, the detectors used in the present invention, such as detectors 525, 530, 535 and 540 use doped silicon junctions, which are less temperature sensitive. Such detectors are known in the art and will not be further described herein.

Gas analyzer 500 also includes optical block 520, which is described in greater detail below in the description of FIG. 9, which shows an exploded perspective view of optical block 520. Optical block 520 has a generally rectangular box form and is positioned over perforation 507D in base plate 506. Optical block 520 has a rectangular perforation (shown in FIG. 9) on its bottom surface for accepting the detector block 524 when the detector block is inserted into perforation 507D.

Optical block 520 is at least partially covered on two of its side surfaces and its top surface by a U-shaped optical block insulator 545. Optical block insulator 545 is made of an insulating material, such as closed-cell foam. Optical block insulator 545 and optical block 520 are covered by optical block cover 550. Optical block cover 550 has generally rectangular box shape and only serves a cosmetic role. Optical block cover 550 fits over the optical block insulator 545 and optical block 520 since the bottom surface of optical block cover 550 is open. Optical block 550 has an opening 551, on its front surface adjacent its non-rectangular side 553, to allow infrared radiation to enter optical block 520. Optical block cover 550 is fastened to optical block 520 by means of screws 552.

Gas analyzer 500 also includes infrared radiation source 515 and sample cell 510. In a preferred embodiment of the present invention, infrared radiation source 515 is an electric heater, an infrared radiation source that is well known to those skilled in the art. In other embodiments, infrared radiation source 515 may be a tungsten filament lamp, such as Carley Lamps, type 214. Sample cell 510 is disposed in front of infrared radiation source 515 to receive infrared radiation emitted therefrom. Sample cell 510 includes end caps 511A and 511B and sample cell tube 512. End caps 511A and 511B are U-shaped and have cylindrical apertures which extend from the front to the back ends of the end caps.

The sample cell tube 512 which is a cylindrical tube made of glass is fitted into the cylindrical apertures of end caps 511A and 511B. The sample cell 510 is secured to the base plate 505 by means of clamps 514 and screws 516. End cap 511B also includes cylindrical extension 517 for accepting gas tubing 585, which in one embodiment sends analyte gas from pump 555 to sample cell 510. In another embodiment, the sample cell 510 receives analyte gas from pump 555 via gas manifolds (shown in FIGS. 6A and 6B) which are molded in base plate 505.

FIG. 5B shows a cut away perspective view of the lower half of sample cell tube 512. As shown in FIG. 5B, the interior surface of the sample cell tube 512 is covered with a reflective coating 518, made of a highly reflective material, such as gold, so as to reduce dissipation of IR radiation entering the sample cell tube 512. At least some of the infrared radiation that strikes reflective coating 518 is reflected onto the infrared radiation path extending along the longitudinal axis 519 of sample cell tube 512. Without the reflective coating, infrared radiation deflected off axis 519 would probably be dissipated as it is unlikely to reenter and be propagated along axis 519.

Additionally, gas analyzer 500 includes transducers 590 for measuring the pressure and temperature of the analyte gas in the gas analyzer 500. Gas analyzer 500 also includes transducer seals 591 disposed above transducers 590. Transducers 590 and transducer seals 591 are well known in the art and, therefore, will not be further described herein.

Moreover, gas analyzer 500 also includes a generally rectangular lower base plate 580. Lower base plate 580 supports detector block 524 which is attached thereto by screws 581. Lower base plate 580 is attached to base plate 505 by means of screws 595 and washers 596.

FIG. 6A shows a bottom plan view of base plate 505. FIG. 6B shows a cross sectional view along line 6B'—6B' in FIG. 6A. As can be seen in FIGS. 6A and 6B, the base plate 505 contains gas manifolds 605, which are molded into base plate 505. The gas manifolds 605 are also herein referred to as gas passages 605. The gas manifolds 605 are U-shaped grooves within the base plate 505. Disposed below gas manifolds 605 are wider grooves 609 for accepting seals 610, which cover and tightly seal the gas manifolds 605. The seals are preferably made of an elastomer such as natural rubber. The gas manifolds 605 act as conduits for transferring gas between elements in the gas analyzer 405. They basically serve the function served by gas tubings in the prior art gas analyzers. Therefore, the location of a particular manifold will depend on the location of the elements which transfer analyte gas by means of the manifold. The gas in the manifolds generally traverse in a horizontal direction. At points where the manifolds are coupled to an element disposed on the base plate 505, a vertically extending cylindrical manifold, such as manifold 615, extends vertically to the top surface of the base plate 505 to transfer gas to the element to which it is coupled. An o-ring, more specifically a face ring 625, is disposed in a circular groove 620 around the manifold 615 so as to preclude leakage of gas as it is transferred between manifold 615 and the element to which it is coupled. The face ring 625 is preferably made of an elastomer such as natural rubber. The use of gas manifolds molded in the base plate 505, reduces the number of components in the apparatus, namely gas tubings. It also improves the reliability of the system as it eliminates the possibility of decoupling gas tubings from the elements to which they are coupled.

FIG. 7A shows a front perspective view of water filter 430 of the present invention. The water filter 430 has a cylindrical body 701 and a cylindrical projection 702 with screw threads 703 disposed on its outer surface for coupling the water filter 430 to the heat sink 431. The water filter 430 also includes openings 704 through which gas enters the water filter 430 and opening 743 through which gas exits the water filter 430. Water filter 430 further includes face rings 708 and 709 to preclude leakage of gas as the gas is transferred between water filter 430 and heat sink 431 to which water filter 430 is coupled.

FIG. 7B shows a cross sectional view of the water filter 430 along line 7B'—7B' of FIG. 7A and the heat sink 431 to which water filter 430 is coupled. FIG. 7C shows a top plan view of the heat sink 431 along line 7C—7C of FIG. 7B. Heat sink 431 is made of a conductive material, such as aluminum, so as to effectively dissipate heat that is transferred to it by the warmer analyte gas. Heat sink 431 comprises a plurality of winding passages 715. The analyte gas enters and exits winding passages 715 through opening 715A and 715B, respectively. In one embodiment, the analyte gas enters a heat sink 431 without being filtered by a particle filter. In another embodiment, a particle filter may be coupled to the heat sink 431 to remove particles from the analyte gas before the gas enters heat sink 431 by way of tube 401B and tube 777 which leads to opening 715A. Removing the particles in the analyte gas reduces the likelihood of clogging the winding passages 715 of the heat sink 431 and the hydrophobic membrane of the water filter 430.

After exiting the heat sink 431 through opening 715B, the gas enters the water filter 430. In the water filter 430 the gas enters into a ringlike cylindrical chamber 720, which on one side is enclosed by the wall 725 of the water filter 430 and on the other side is enclosed by a hydrophobic membrane 730. The hydrophobic membrane 730 prevents the passages of water molecules from chamber 720 to chamber 740, a cylindrical chamber whose circular surface is defined by the hydrophobic membrane 730. From chamber 740 gas travels to tube 741 from which it exits through opening 743. From opening 743 the gas enters tube 798 which is coupled to tube 501 which is in turn coupled to gas analyzer 405.

Water collected in chamber 720 exits the water filter 430 through opening 736 disposed on the back side of water filter 430. Opening 736 can be closed by positioning lid 737 such that it covers opening 736. FIG. 7D shows a rear perspective view of the water filter 430. FIG. 7D shows lid 737 and knob 738 to which lid 737 is coupled.

Therefore, by use of the hydrophobic membrane which blocks the passages of water, the water filter 430 removes water from the gas to be analyzed before the gas enters the gas analyzer 405. Removing the water from the analyte gas prior to its entrance into the gas analyzer reduces the possibility of damaging the gas analyzer components by water molecules, which can facilitate corrosion of the gas analyzer components. Additionally, it improves the accuracy of the measurements by the gas analyzer since the water molecules can affect measurements in the system.

The water filter 430 and heat sink 431 are particularly useful when used in conjunction with a gas analyzer that measures the concentration of gases in a gas sample having a high temperature and relatively high water concentration. Thus, the water filter 430 and heat sink 431 are particularly useful when the gas analyzer is used to measure the concentration of gases in a motor vehicle exhaust which, as is well known in the art, tends to have a high temperature and a relatively high water concentration. Similarly, it may be useful to include a particle filter 425 to remove particulate matter from the gas before it enters into the heat sink 431 and water filter 430.

FIG. 8 shows a schematic diagram of the gas path for a gas analyzed by the gas analyzer module set 400 of the present invention. In one embodiment, the gas to be analyzed is first passed through a particle filter 425 which removes particulate matter from the gas. The gas exiting the particle filter 425 then enters the heat sink 431 which reduces the temperature of the gas. In another embodiment, which does not include particle filter 425, the gas to be analyzed is sent to the heat sink 431 without being filtered. After passing through the heat sink 431, the gas enters the water filter 430, which removes water molecules from the gas prior to its entrance into the gas analyzer. The gas exiting the water filter 430 enters pump 555, which pumps the gas to the sample cell tube 512 shown in FIG. 5A. The gas is pumped into the gas analyzer rather than drawn in by suction so as to reduce the infusion of other gases into the gas analyzer through possible leaks in the system. In one embodiment of the present invention, the gas exiting the gas pump 555 enters a gas tube (not shown) which is coupled to gas passages 605 molded in the base plate 505. Gas manifolds 605 molded into the base plate 505 are shown in FIGS. 6A and 6B and are described in greater detail above. In another embodiment, gas tube 585 directly couples the pump 555 to the sample cell tubing 512. After passing through the sample cell tube 510 for IR analysis, the gas enters the $O_2$ chemical cell 575 and the $NO_x$ chemical cell 570. Upon exiting the chemical cells the gas is passed to exhaust 435 from which it exits the gas analyzer module set 400. While in the sample cell tube 512, the gas is radiated with infrared (IR) radiation from the IR radiation source 515. IR radiation that is not absorbed by gases in the sample cell tube or system sensitive producing elements exits the sample cell tube 512 and is transmitted to the optical block 520.

FIG. 9 shows an exploded perspective view of the optical block 520 shown in FIG. 5. Optical block 520 includes optical housing 905 within which the optical elements of the gas analyzer 500 are disposed. Optical housing 905 is fabricated from one material, such as plastic or glass, such that thermal and mechanical disturbances to which the optical block 520 is subjected equally shift each of the optical components so as to maintain the relative position of the components. Optical housing 905 is assembled by aligning and attaching segments 906A and 906B. Segments 906A and 906B are attached to each other by means of screws inserted into apertures 975. Segments 906A and 906B have corresponding diagonal slots 907A, 907B, 907C and 907D and horizontal slots 908A, 908B, 908C and 908D for accepting optical elements, such as beam splitters (both neutral density beam splitters and dichroic filters), narrow band pass filters and mirrors. The interior IR radiation reflecting surfaces of the optical housing, such as surface 910, are coated with a highly reflective material, such as gold, so as to reduce IR radiation losses in the system. At least some of the deflected IR radiation strikes the highly reflective material covering the IR reflecting surfaces, such as surface 910, and reenters the IR radiation axis 965 and is detected by one of the detectors 525, 530, 535 and 540. Incoming IR radiation from sample cell tube 510 enters the optical block 520. Optical block 520 also includes a mirror 920 which reflects the IR radiation that enters the optical block 520 so that the IR radiation is transmitted on an axis along which the optical filters are disposed. The optical block is fixed to the base plate 505 by means of screws 552 (shown in FIG. 5) inserted through apertures 980. Aperture 985 is also used for attaching the optical block 520 to the base plate 505 via attachment to detector block 540.

The IR radiation reflected by mirror 920 passes through beam splitter 925, which is a neutral density beam splitter, and, therefore, reflects approximately 50% of the incident energy and transmits approximately 50% of the incident energy. Beam splitter 925 is fitted into slot diagonal 907A. Beam splitter 925 has an incident surface which forms a 45 degree angle with the incident IR radiation axis 965. The reflected and transmitted portions of the incident IR radiation are substantially identical in that they span substantially the same energy spectrum and contain substantially the same amount of energy. The IR radiation reflected by the beam splitter 925 is intercepted by narrow band pass filter 930, which only passes IR energy within a wavelength band corresponding to the absorption band for $CO_2$. Narrow band pass filter 930 is fitted into horizontal slot 908A. The IR radiation transmitted by narrow band pass filter 930 is sent to detector 525 (shown in FIG. 5) for determining the concentration of $CO_2$.

The IR radiation transmitted by beam splitter 925 is intercepted by dichroic filter 940. Dichroic filter 940, like beam splitter 925, is oriented such that its incident surface forms a 45% angle with respect to the incident IR radiation axis 965. Thus, the dichroic filter 940 is set parallel to the beam splitter 925. Dichroic filter 940 is fitted into diagonal slot 907B. Dichroic filter 940 reflects IR radiation above a certain wavelength and transmits IR radiation below another wavelength. As can be seen in FIG. 11, the dichroic filter 940 does not have a narrow transition band above and below which IR radiation is reflected and transmitted, respectively. Instead, dichroic filter 940 has a wide transition band 1105 in which a portion of the radiation of a given wavelength is transmitted while another portion of the radiation of the same given wavelength is reflected. Outside the wide transition band, IR radiation is almost entirely either reflected or transmitted. The IR radiation reflected by dichroic filter 940 is transmitted to the narrow band pass filter 945, which is fitted into horizontal slot 908B. Narrow band pass filter 945 transmits IR radiation corresponding to the absorption band for CO and reflects IR radiation falling outside the absorption band for CO. The IR radiation passing through the narrow band pass filter 945 is transmitted to detector 530 (shown in FIG. 5) for determining the concentration of CO.

The IR radiation that passes through dichroic filter 940 is transmitted to optical filter 950. Optical filter 950 is also oriented such that its incident surface forms a 45 degree angle with the incident IR radiation axis 965. In other words, optical filter 950 is set parallel to the beam splitter 925 and the dichroic filter 940. Optical filter 950 is fitted into diagonal slot 907C. Because optical filter 950 is oriented such that its incident surface is disposed at a 45 degree angle with respect to the incident IR radiation axis 965, optical filter 950 reflects some of the incoming IR radiation along an axis that is normal to the incident IR radiation axis 965 and transmits IR radiation along an axis that is coincident with the incident IR radiation axis 965. Optical filter 950 is optically coated so as to selectively transmit only IR radiation within a band pass. The optical coating used on optical filter 950 is well known in the art and is commonly used to coat narrow band pass optical filters. Because of the optical coating, optical filter 950 acts as a narrow band pass filter, passing IR radiation within a narrow band pass, and reflecting IR radiation outside said narrow band pass.

In effect, optical filter 950 is an ordinary narrow band pass filter which has been positioned at 45 degrees with respect to the axis of incident IR radiation whereas, in the prior art, narrow band pass filters are normally set at 90 degrees with respect to the axis of incident IR radiation. The novel positioning of a narrow band pass filter, such as optical filter 950, allows, in a beam splitter IR analyzer, the placement of the reference transmission band in the spectral separation between two regions of spectral interest even though the spectral separation is too narrow to fit both the reference transmission band and the transition band of a dichroic filter. More specifically, it allows using a reference transmission band between the absorption bands of $CO_2$ and HCs, which was before the present invention considered impossible in beam splitter IR analyzers because the separation between the absorption bands of $CO_2$ and HCs is not wide enough to fit a reference transmission band and the transition band of a dichroic filter. Using a transmission band between the absorption bands of $CO_2$ and HCs makes the reference reading a more accurate reference reading than it otherwise would be if the reference transmission band was placed further away from the absorption bands of the gases of interest.

The IR radiation reflected by optical filter 950 is transmitted to narrow band pass filter 955, which transmits IR radiation having wavelengths within the absorption band for hydrocarbons (HCs). Narrow band pass filter 955 is fitted into horizontal slot 908C. The IR radiation that passes through narrow band pass filter 955 is transmitted to detector 535 (shown in FIG. 5) for determining the concentration of HCs.

In a preferred embodiment, the IR radiation that is transmitted by the optical filter 950 is transmitted to mirror 960, which is fitted into diagonal slot 907D. Mirror 960 is positioned at a 45 degree angle with respect to the incident IR radiation axis 965. Therefore, it reflects the incident IR radiation to an axis perpendicular to the incident IR radiation axis 965. The IR radiation is reflected to reference detector 540 (shown in FIG. 5). In another embodiment, the reference detector may be positioned directly behind the optical filter 950 so as to directly receive the IR radiation passing through optical filter 950. In such an embodiment, there would be no need for mirror 960. The reference detector 540 receives IR radiation within the reference transmission band which falls between the absorption bands for $CO_2$ and HCs. Use of a reference transmission band that is in close proximity to the absorption bands of the gases of interest but does not extend into the absorption bands of the gases of interest, allows the reference detector 540 to more accurately reflect the system sensitivities to IR radiation of wavelengths corresponding to the absorption wavelengths of the gases of interest. Since optical filter 950 acts as a narrow band pass filter for IR radiation having wavelengths within the reference transmission band, there is no need for using an additional narrow band pass filter that would otherwise be fitted within slot 908D. In another embodiment, however, one may use such a filter to refilter the IR radiation reflected by mirror 960 before it is transmitted to detector 540.

FIG. 12 shows a graph of the absorption bands for the gas of interest, CO, $CO_2$ and HCs, and the reference transmission band. As can be seen in FIG. 12, the reference transmission band 1205 is placed between the absorption band for $CO_2$ 1210 and the absorption band for HCs 1215. The placement of the reference transmission band 1205 between the absorption bands 1210 & 1215 for $CO_2$ and HC, respectively, is made possible by the sharp cutoff, i.e. narrow transition band, between the transmission and reflection regions provided by the optical filter 950 which acts both as a narrow band pass filter and a beam splitter. It will be appreciated by those skilled in the art that a reference transmission band 1205, which is placed between the absorption bands 1210 & 1215 for $CO_2$ and HCs, respectively, and does not overlap either one, provides a more accurate measure of the system sensitivities than a reference transmission band placed farther away from the absorption bands of the gases of interest.

FIG. 10 shows a schematic diagram of the optical filters and detectors of the present invention. Many of the elements in FIG. 10 are also shown in FIG. 9 and are, therefore, referenced with the same reference numbers used in FIG. 9. The incident IR radiation AI is transmitted to the beam splitter 925 (a neutral density beam splitter), which reflects approximately 50% of AI as BR and transmits approximately 50% of AI as BI. As shown in FIG. 10, the beam splitter 925 forms a 45 degree angle with the axis of the incident IR radiation, AI. As a result, the reflected IR radiation, BR, has an axis of propagation that is normal to the axis of the incident IR radiation, AI, while the transmitted IR radiation, BI, has an axis of propagation that is coincident with the axis of propagation for AI. BR than passes through the $CO_2$ narrow band pass filter 930 which passes IR radiation corresponding to the absorption band for $CO_2$. The IR radiation BRP that passes through the $CO_2$ narrow band pass filter 930 is transmitted to the $CO_2$ detector 525. BI, on the other hand, is transmitted to the dichroic filter 940 which forms a 45 degree angle with the axis of the incident IR radiation, BI, and is set parallel to the beam splitter 925. The dichroic filter 940 reflects IR radiation CR and transmits IR radiation CI. CR has a propagation axis that is perpendicular to that of BI and contains mostly IR radiation having wavelengths within the reflection band and some IR radiation having wavelengths within the transition band of the dichroic filter 940. On the other hand, CI has a propagation axis that is coincident with the axis of propagation for BI and contains mostly IR radiation having wavelengths within the transmission band and some IR radiation having wavelengths within the transition band of the dichroic filter 940. CR includes IR radiation within the absorption band for CO. CR is transmitted to the CO narrow band pass filter 945, which transmits IR radiation corresponding to the absorption band for CO. The IR radiation, CRP, that passes through the CO narrow band pass filter 945 is transmitted to the CO detector 530. CI is transmitted to the optical filter 950, which forms a 45 degree angle with the axis of the incident IR radiation, CI, and is parallel to the dichroic filter. The optical filter 950 transmits IR radiation, DI, corresponding to the reference transmission band. In a preferred embodiment, DI is reflected off of mirror 960, which is disposed at a 45 degree angle with respect to the axis of propagation for DI. Consequently, DI is reflected to an axis that is normal to the axis of propagation of DI prior to its reflection by the mirror 960. The IR radiation reflected by the mirror 960 is transmitted to the reference detector 540. DR, the portion of CI reflected by optical filter 950, has an axis of propagation that is normal to that of CI and is transmitted to an HC narrow band pass filter 955 which passes IR radiation corresponding to the absorption band for HCs. The IR radiation, DRP that passes through the HC narrow band pass filter 955 is transmitted to the HC detector 535.

It will be appreciated by those of ordinary skill in the art that the arrangement of the optical elements in the present invention, particularly that of the optical filter 950 allows picking off nearly all of the incident IR radiation energies within a band of interest, i.e., having a wavelength that falls within a wavelength band of interest, and transmitting nearly all of the incident IR radiation (i.e. nearly a 100%) that falls outside the energy band of interest. For example, optical filter 950 passes nearly a 100% of the incident IR radiation having wavelengths corresponding to the reference transmission band. Similarly, optical filter 950 reflects nearly a 100% of the incident IR radiation that falls outside the reference transmission band and includes IR radiation that falls within the absorption band for HCs. The filter may not achieve 100% reflection because of absorption of radiation by the coating materials. Transmission in the pass band regions of narrow band pass filters typically lies between 70 and 90 percent, with the remaining energy being reflected due to the actual thickness of many dozens of coating layers not being precisely the same as the theoretical thicknesses required to eliminate all reflection. The optical filter 950 of the present invention allows separating the incident IR radiation into a reflection band and a transmission band with a narrow transition band of only 0.16 μm at 3.64 μm.

It is also to be noted that if a neutral density beam splitter, such as beam splitter 925, were used instead of the optical filter 950, then only 50% (or less due to inherent beam splitter inefficiencies) of the incident energy having wavelengths of interest for analysis at a first stage would be transmitted to that first stage and only 50% (or less due to inherent beam splitter inefficiencies) having wavelengths of interest for analysis at a second stage would be reflected to that second stage. Thus, in a system using a neutral density beam splitter instead of optical filter 950, the signal level would be lower than that in the system of the present invention by approximately a factor of 2. Thus, the S/N ratio in the present invention is twice as large as the S/N in a system that uses a second neutral density beam splitter instead of optical filter 950.

FIG. 11 shows the transmission and reflection characteristics of the dichroic filter 940. Dichroic filter 940 does not provide a sharp cutoff wavelength above which IR radiation is clearly transmitted and below which IR radiation is clearly reflected. Instead, there is a wide roll off range, i.e. a wide transition band 1105 of approximately 0.4 μm at 4.25 μm, in which some of the IR energy is reflected and some is transmitted. Substantially all the IR radiation having a wavelength greater than the upper limit of the roll off range, is reflected while substantially all of the IR radiation wavelength having a wavelength less than the lower limit of the roll off range, is transmitted. The relatively long roll off range is a common feature of dichroic filters in general and is not a distinctive feature of dichroic filter 940 used in the present invention. The long roll off range of a dichroic filter makes it impossible to use a dichroic filter together with a narrow band pass reference filter between the absorption bands of HCs and $CO_2$.

The use of the optical filter 950 as oriented in the present invention, the optical housing 905 with internal IR reflective surfaces coated with a highly reflective material, the coating of the interior surface of the sample cell tube 510 with a highly reflective material, as well as other features and elements of the present invention, allows using an IR radiation of considerably lower intensity than those used in the prior art. The energy savings in the different stages of the gas analyzer of the present invention allow operating the entire gas analyzer including the pump 555, in any given application, with considerably less power than otherwise. For example, a typical prior art NDIR automotive gas analyzer would require at least 20 watts for operation whereas the present invention uses less than 6 watts.

While the present invention has been particularly described with respect to the illustrated embodiments, it will be appreciated that various alterations, modifications and adaptations may be made based on the present disclosure, and are intended to be within the scope of the present invention. While the invention has been described in connection with what is presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. An infrared analyzer comprising:
   a source of infrared radiation, said source emanating infrared radiation onto an infrared radiation path;
   a sample cell for containing an analyte gas, said sample cell being interposed in the path of infrared radiation emanating from said source; and
   detector means positioned in the path of infrared radiation after passing through said sample cell for providing an indication of the absorption of infrared radiation by the analyte gas, said detector means including:
      a first infrared radiation detector;
      a second infrared radiation detector; and
      at least one narrow band pass optical filter oriented to transmit infrared radiation within a narrow wavelength band to said first infrared radiation detector and to reflect infrared radiation outside of the narrow wavelength band to said second infrared radiation detector, whereby said first infrared radiation detector provides an indication of infrared radiation absorption by the analyte gas within the narrow wavelength band and wherein said second infrared radiation detector provides an indication of infrared radiation absorption by the analyte gas outside of the narrow wavelength band.

2. The infrared analyzer of claim 1, wherein infrared radiation incident to said at least one optical filter defines an incident infrared radiation axis, and wherein said at least one optical filter comprises an incident surface which is disposed at a 45 degree angle with respect to said incident infrared radiation axis.

3. The infrared analyzer of claim 2, wherein said narrow band pass optical filter has a pass band located between the infrared radiation absorption bands for hydrocarbons and carbon dioxide.

4. An infrared analyzer comprising:
   a source of infrared radiation, said source emanating infrared radiation onto an infrared radiation path;
   a sample cell for containing an analyte gas, said sample cell being interposed in the path of infrared radiation emanating from said source;
   at least one optical element which receives infrared radiation after the infrared radiation passes through said sample cell;
   an optical housing for holding said at least one optical element, said housing having an interior surface, wherein said at least one optical element is disposed within said optical housing;
   at least one infrared radiation reflecting surface on said interior surface of said optical housing, wherein said at least one infrared radiation reflecting surface is coated with a highly reflective material; and
   at least one infrared radiation detector for providing an indication of the absorption of infrared radiation by the analyte gas, said at least one infrared radiation detector receiving infrared radiation from said at least one optical element.

5. The infrared analyzer of claim 4 comprising a plurality of optical filters disposed within said optical housing, each of said optical filters having a relative position with respect to other optical filters within said optical housing, wherein said optical housing is fabricated from one material such that thermal and mechanical disturbances substantially equally shift each of the optical filters so as to maintain the relative position of each of said optical filters with respect to the other optical filters within said optical housing.

6. The infrared analyzer of claim 5, wherein said optical housing is fabricated from plastic.

7. The infrared analyzer of claim 4, wherein said highly reflective material is gold.

8. A gas analyzer comprising:
 a gas inlet wherein an analyte gas enters the gas analyzer;
 a base plate having gas passages molded therein, said gas passages coupled to said gas inlet;
 a source of radiation, said source emanating radiation onto a radiation path;
 a sample cell for containing at least a portion of the analyte gas, wherein said sample cell is coupled to said gas passages and is interposed in the path of radiation emanating from said source; and
 at least one detector for providing an indication of the absorption of radiation by the analyte gas, said at least one detector receiving radiation after the radiation has passed through said sample cell.

9. The gas analyzer of claim 8 further comprising a seal disposed on at least one of said gas passages to reduce gas leakage from said gas passages.

10. An infrared analyzer comprising:
 a source of infrared radiation, said source emanating infrared radiation onto a infrared radiation path;
 a sample cell for containing an analyte gas, said sample cell interposed in the path of infrared radiation emanating from said source;
 a first optical element to transmit a first portion of infrared radiation that said first optical element receives from said sample cell and reflect a second portion of the infrared radiation that said first optical element receives from said sample cell, wherein the first portion and the second portion each comprise a substantially identical energy spectrum;
 a first narrow band pass filter receiving the first portion;
 a first detector detecting infrared radiation that passes through said first narrow band pass filter;
 a second optical element, said second optical element receiving the second portion, reflecting substantially all infrared radiation within the second portion having a wavelength above a first predefined wavelength and transmitting substantially all infrared radiation within the second portion having a wavelength below a second predefined wavelength, wherein the first predefined wavelength is greater than the second predefined wavelength;
 a second narrow band pass filter receiving infrared radiation reflected by said second optical element;
 a second detector detecting infrared radiation that passes through said second narrow band pass filter;
 a third optical element, said third optical element receiving infrared radiation transmitted by said second optical element, transmitting substantially more than 50% of the infrared radiation received from said second optical element having a wavelength within a narrow band pass and reflecting substantially more than 50% of the infrared radiation received from said second optical element having a wavelength outside the narrow band pass;
 a third narrow band pass filter receiving the infrared radiation reflected by said third optical element;
 a third detector detecting infrared radiation that passes through said third narrow band pass filter; and
 a fourth detector detecting infrared radiation transmitted by said third optical element.

11. The infrared analyzer of claim 10 further comprising a mirror for reflecting infrared radiation transmitted by said third optical element to said fourth detector.

12. The infrared analyzer of claim 11 further comprising an electronic board, wherein all the detectors are plugged into said electronic board.

13. A gas analyzer module set comprising:
 means for inputting data;
 a processor coupled to said inputting means;
 means for outputting data coupled to said processor; and
 an non-dispersive infrared (NDIR) analyzer coupled to said processor, wherein said NDIR analyzer comprises:
  a source of infrared radiation, said source emanating infrared radiation onto an infrared radiation path;
  a sample cell for containing an analyte gas, said sample cell interposed in the path of infrared radiation emanating from said source; and
  a first infrared radiation detector;
  a second infrared radiation detector;
  at least one optical filter for receiving at least a portion of the infrared radiation that passes through said sample cell, wherein said at least one optical filter is oriented to transmit infrared radiation within a narrow wavelength band to said first infrared radiation detector and to reflect infrared radiation outside of the narrow wavelength band to said second infrared radiation detector.

14. The gas analyzer module set of claim 13, wherein said NDIR analyzer comprises:
 a first optical element to transmit a first portion of infrared radiation that said first optical element receives from said sample cell and reflect a second portion of the infrared radiation that said first optical element receives from said sample cell, wherein the first portion and the second portion each comprise a substantially identical energy spectrum;
 a first narrow band pass filter receiving the first portion;
 a first detector detecting infrared radiation that passes through said first narrow band pass filter;
 a second optical element, said second optical element receiving the second portion, reflecting substantially all infrared radiation within the second portion having a wavelength above a first predefined wavelength and transmitting substantially all infrared radiation within the second portion having a wavelength below a second predefined wavelength, wherein the first predefined wavelength is greater than the second predefined wavelength;
 a second narrow band pass filter receiving infrared radiation reflected by said second optical element;
 a second detector detecting infrared radiation that passes through said second narrow band pass filter;
 a third optical element, said third optical element receiving infrared radiation transmitted by said second optical element, transmitting substantially more than 50% of the infrared radiation received from said second optical element having a wavelength within a narrow band pass and reflecting substantially more than 50% of the infrared radiation received from said second optical element having a wavelength outside the narrow band pass;

a third narrow band pass filter receiving said infrared radiation reflected by said third optical element;

a third detector detecting infrared radiation that passes through said third narrow band pass filter; and a fourth detector detecting infrared radiation transmitted by said third optical element.

15. The gas analyzer module set of claim 14, wherein said NDIR analyzer further comprises:

an optical housing for housing said first optical element, said first narrow band pass filter, said second optical element, said second narrow band pass filter, said third optical element and said third narrow band pass filter, wherein interior IR radiation reflecting surfaces of said optical housing are coated with a highly reflective material.

16. The gas analyzer module set of claim 15 further comprising a water filter for filtering water from the analyte gas prior to the analyte gas entering into the NDIR analyzer, said water filter comprising:

an inlet for receiving the analyte gas;

a hydrophobic membrane receiving the analyte gas from the inlet and removing water therefrom; and an outlet for receiving the analyte gas after it passes through the hydrophobic membrane, wherein the analyte gas from the outlet is transferred to the NDIR analyzer.

17. The gas analyzer module set of claim 13 further comprising a base plate having gas passages molded therein, wherein said NDIR analyzer is disposed on said base plate.

18. A gas analyzer comprising:

a source of radiation, said source emanating radiation onto a radiation path;

a water filter comprising an inlet, an outlet and a hydrophobic membrane disposed between said inlet and said outlet, said water filter receiving a sample gas at said inlet, removing water from the sample gas at said hydrophobic membrane and thereafter transferring the sample gas through said outlet;

a sample cell for containing at least a portion of the sample gas received from the water filter and receiving radiation from said radiation source, wherein part of the radiation received by said sample cell is absorbed by the sample gas; and at least one detector for providing an indication of the absorption of radiation by the sample gas, wherein said at least one detector receives radiation that passes through said sample cell.

19. A water filter for use in a gas analyzer, wherein said water filter comprises:

an inlet for receiving an analyte gas;

a hydrophobic membrane for receiving the analyte gas from the inlet and removing water therefrom; and an outlet for receiving the analyte gas after it passes through the hydrophobic membrane.

* * * * *